United States Patent [19]

Shetty et al.

[11] 4,420,487
[45] Dec. 13, 1983

[54] DIURETIC AND ANTIHYPERTENSIVE BENZIMIDAZOLES

[75] Inventors: Bola V. Shetty, Stamford, Conn.; Arthur McFadden, East Brunswick, N.J.

[73] Assignee: The Purdue Frederick Company, Norwalk, Conn.

[21] Appl. No.: 164,554

[22] Filed: Jun. 30, 1980

Related U.S. Application Data

[63] Continuation-in-part of Ser. No. 895,048, Apr. 10, 1978, abandoned.

[51] Int. Cl.³ .................. A61K 31/415; C07D 235/04; C07D 231/42; C07D 263/50
[52] U.S. Cl. ................................ 424/273 B; 548/306; 548/327; 548/330; 548/331; 548/332; 548/333; 548/334; 260/239.9
[58] Field of Search ............... 548/306, 327, 330, 331, 548/332, 333, 334; 424/273 B

[56] References Cited

U.S. PATENT DOCUMENTS 3,823,154 7/1974 Corbett et al. ..................... 548/306

OTHER PUBLICATIONS

Yale, Journal of Medicinal & Pharmeceutical Chemistry, vol. 1, No. 2, 1959.
Widdig, et al., Chem. Absts., 79:115589x.

Primary Examiner—Henry R. Jiles
Assistant Examiner—Robert C. Whittenbaugh
Attorney, Agent, or Firm—Steinberg & Raskin

[57] ABSTRACT

The invention relates to compounds which exhibit diuretic and antihypertensive properties and have the following structures:

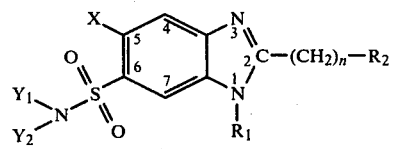

or

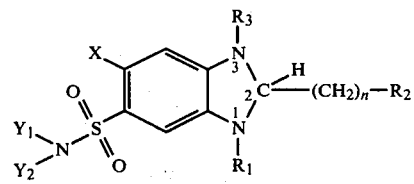

or pharmaceutically acceptable salts thereof, wherein:
X = halogen or trifluoromethyl
$Y_1$ and $Y_2$ = independently hydrogen, alkyl, acyl, aryl, substituted aryl or heterocycle,
$R_1$ = hydrogen, lower alkyl, aryl, substituted aryl, benzyl, substituted benzyl, aralkyl, heterocycle or substituted heterocycle,
n = 0 or an integer from 1–4
$R_2$ = amino, substituted amino, guanidino, substituted guanidino, halogen, alkyl, substituted alkyl, aryl, substituted aryl or heterocycle, and
$R_3$ = hydrogen, lower alkyl, aryl, substituted aryl, benzyl, substituted benzyl, aralkyl, heterocycle, substituted heterocycle or acyl.

17 Claims, No Drawings

DIURETIC AND ANTIHYPERTENSIVE BENZIMIDAZOLES

CROSS REFERENCE TO RELATED APPLICATION

This application is a continuation-in-part of our co-pending application Ser. No. 895,048, filed Apr. 10, 1978, for "Benzimidazole and Benzimidazolidine Derivatives with Diuretic and Antihypertensive Activity", now abandoned.

BACKGROUND OF THE INVENTION

A new class of compounds exhibiting diuretic and antihypertensive properties are produced by various methods based upon known types of reactions.

SUMMARY OF THE INVENTION

The invention generally relates to compounds having diuretic and antihypertensive properties and which have the following structural formulas:

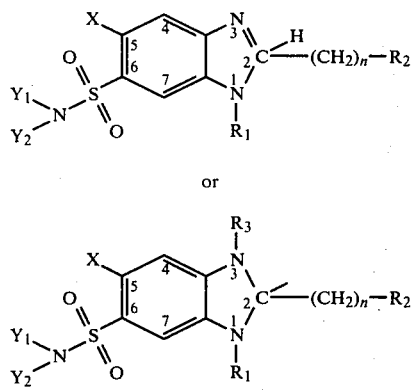

or or pharmaceutically acceptable salts thereof, wherein:
X = halogen or trifluoromethyl
$Y_1$ and $Y_2$ = independently hydrogen, alkyl, acyl, aryl, substituted aryl or heterocycle,
$R_1$ = hydrogen, lower alkyl, aryl, substituted aryl, benzyl, substituted benzyl, aralkyl, heterocycle or substituted heterocycle,
n = 0 or an integer from 1–4
$R_2$ = amino, substituted amino, guanidino, substituted guanidino, halogen, alkyl, substituted alkyl, aryl, substituted aryl or heterocycle, and
$R_3$ = hydrogen, lower alkyl, aryl, substituted aryl, benzyl, substituted benzyl, aralkyl, heterocycle, substituted heterocycle or acyl.

The above substituents preferably have the following definitions:
X = halogen or trifluoromethyl,
$Y_1$ and $Y_2$ = independently hydrogen, or lower alkyl,
$R_1$ = hydrogen, lower alkyl, phenyl or substituted phenyl substituted by lower alkyl, lower alkoxy or halogen,
n = 0 or an integer from 1–4,
$R_2$ = hydrogen, hydroxyl, mercapto, lower alkyl mercapto, furyl, adamantanyl, halogen, lower alkyl, phenyl, phenyl substituted by lower alkyl, phenyl substituted by halogen, biphenyl, formamido, guanidino, guanidino substituted by lower alkyl and amino substituted by lower alkyl, by carboxy, by carboxy-lower alkyl, by lower alkyl-carboxy, by phenyl, by phenyl substituted by carboxy, by phenyl substituted by hydroxy, by phenyl substituted by lower alkyl, by phenyl substituted by halogen, by furfuryl, and by carboxy substituted by phenoxy lower alkyl, and
$R_3$ = hydrogen, lower alkyl, phenyl or substituted phenyl substituted by lower alkyl, lower alkoxy or halogen.

It is a primary object to provide for new compounds of the above structure.

It is a further object of the present invention to provide for methods of producing the above compounds.

It is yet a further object of the present invention to provide a new class of compounds which exhibit diuretic and antihypertensive activity.

Other objects and advantages of the present invention will be apparent from a further reading of the specification and of the appended claims.

The production of the compounds of the present invention may be effected by various methods which are known in principle. The following illustrates two different convenient syntheses which may be used in the production of the compounds of the invention:

PREPARATION OF 2-AMINO-5-CHLORO-6-SULFAMYL-1H—BENZIMIDAZOLE HYDROBROMIDE (VII)

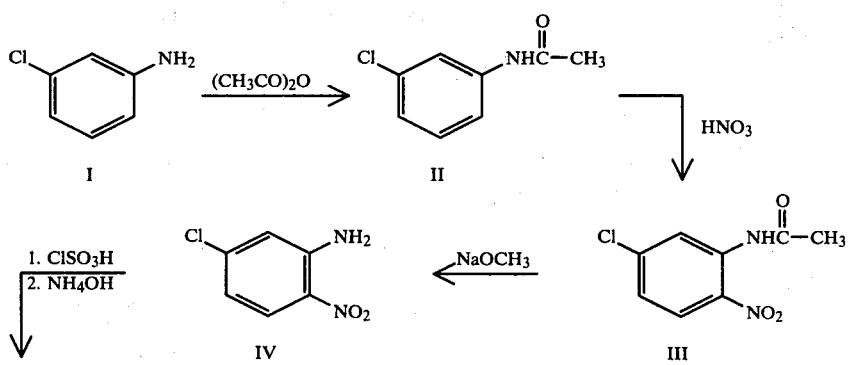

PREPARATION OF 2-AMINO-5-CHLORO-6-SULFAMYL-1H—BENZIMIDAZOLE HYDROBROMIDE (VII)

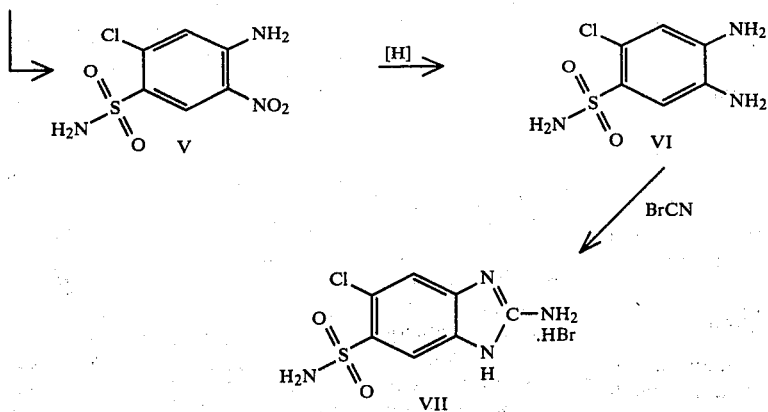

PREPARATION OF 5-CHLORO-2-GUANIDINO-6-SULFAMYL-1H—BENZIMIDAZOLE HYDROCHLORIDE (VIII)

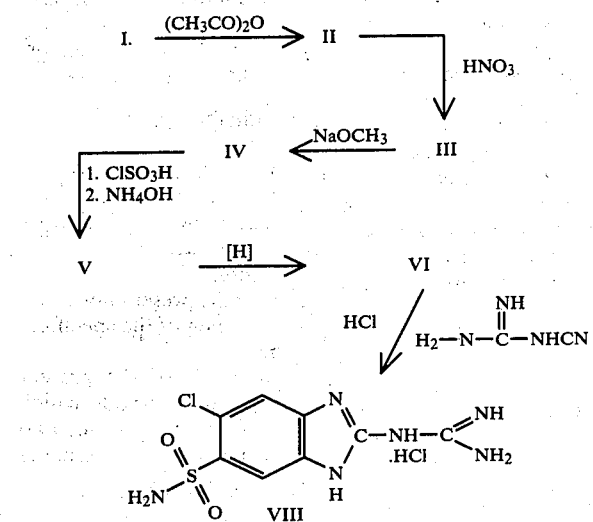

As indicated above, in the structural formulas of the invention which were illustrated X is a halogen or trifluoromethyl.

$Y_1$ and $Y_2$ are each hydrogen, alkyl, acyl, aryl, substituted aryl or heterocycle. More preferably $Y_1$ and $Y_2$ are each either hydrogen and/or lower alkyl.

The substituent $R_1$ may be hydrogen, lower alkyl, aryl, substituted aryl, benzyl, substituted benzyl, aralkyl, heterocycle or substituted heterocycle. More preferably $R_1$ is hydrogen, lower alkyl, aryl or substituted aryl, preferably substituted by lower alkyl, alkoxy, or halogen.

As indicated "n" may be 0 or an integer from 1–4. Most preferably "n"=0.

$R_2$ may be amino, substituted amino, guanidino, substituted guanidino, halogen, alkyl, substituted alkyl, aryl substituted aryl or heterocycle. Most preferably $R_2$ is amino, substituted amino substituted by lower alkyl or guanidino.

The substituent $R_3$ may be hydrogen, lower alkyl, aryl, substituted aryl, benzyl, substituted benzyl, aralkyl, heterocycle, substituted heterocycle or acyl. More preferably $R_3$ is hydrogen or lower alkyl.

In addition to compounds (VII) and (VIII) shown above, other specific suitable compounds of the above formula include:

5-chloro-2-formamido-6-sulfamyl-1H-benzimidazole
2-carbethoxyamino-5-chloro-6-sulfamyl-1H-benzimidazole
2-benzylamino-5-chloro-6 sulfamyl-1H-benzimidazole
5-chloro-6-N,N-dimethylsulfonamido-2-guanidino-1H-benzimidazole
5-chloro-2-guanidino-6-N-methylsulfonamido-1H-benzimidazole
2-amino-5-chloro-6-sulfamyl-1-(o-tolyl)-1H-benzimidazole
2-amino-5-chloro-1-(o-methylbenzyl)-6-sulfamyl-1H-benzimidazole
5-chloro-2-dimethylamino-6-sulfamyl-1H-benzimidazole
2-dimethylamino-6-sulfamyl-5-trifluoromethyl-1H-benzimidazole
2-acetamido-5-chloro-6-sulfamyl-1H-benzimidazole
5-chloro-2-guanidino-1-methyl-6-sulfamyl-1H-benzimidazole
2-acetimido-5-chloro-6-sulfamyl-1H-benzimidazole
2-carbethoxyamino-5-chloro-6-sulfamyl-1H-benzimidazole
2-formamido-6-sulfamyl-5-trifluoromethyl-1H-benzimidazole
2-carbethoxyamino-6-sulfamyl-5-trifluoromethyl-1H-benximidazole
2-benzylamino-5-bromo-6-sulfamyl-1H-benzimidazole
5-chloro-2-(2,6-dichloro) anilino-6-sulfamyl-1H-benzimidazole
2-(2,6-dichloro) anilino-6-sulfamyl-5-trifluoromethyl-1H-benzimidazole
5-bromo-2-(2,6-dichloro) anilino-6-sulfamyl-1H-benzimidazole
5-chloro-2-(2,6-dimethyl) anilino-6-sulfamyl-1H-benzimidazole
2-(2,6-dimethyl) anilino-6-sulfamyl-5-trifluoromethyl-1H-benzimidazole
5-bromo-2-(2,6-dimethyl) anilino-6-sulfamyl-1H-benzimidazole 2-amino-6-sulfamyl-5-trifluoromethyl-1H-benzimidazole
2-amino-5-bromo-6-sulfamyl-1H-benzimidazole
2-guanidino-6-sulfamyl-5-trifluoromethyl-1H-benzimidazole
5-bromo-2-guanidino-6-sulfamyl-1H-benzimidazole
5-chloro-2-guanidino-6-N-methylsulfonamido-1H-benzimidazole
2-amino-5-chloro-6-N-methylsulfonamido-1H-benzimidazole
2-amino-6-N-methylsulfonamido-5-trifluoromethyl-1H-benzimidazole
2-amino-5-chloro-6-N,N-dimethylsulfonamido-1H-benzimidazole
2-guanidino-6-N-methylsulfonamido-5-trifluoromethyl-1H-benzimidazole
5-bromo-2-guanidino-6-N methylsulfonamido-1H-benzimidazole
6-N,N-dimethylsulfonamido-2-guanidino-5-trifluoromethyl-1H-benzimidazole
5-bromo-6-N,N-dimethylsulfonamido-2-guanidino-1H-benzimidazole
5-fluoro-2-guanidino-6-sulfamyl-1H-benzimidazole
2-amino-5-fluoro-6-sulfamyl-1H-benzimidazole
5-chloro-2-[4-(2,3-dichlorophenoxymethylcarboxy)]amino-6-sulfamyl-1H-benzimidazole
2-[4-(2,3-dichlorophenoxymethylcarboxy)] amino-6-sulfamyl-5-trifluoromethyl-1H-benzimidazole
5-bromo-2-[4-(2,3-dichlorophenoxymethylcarboxy)] amino-6-trifluoromethyl-1H-benzimidazole
2-amino-5-chloro-6-sulfamylbenzimidazolidine
2-amino-6-sulfamyl-5-trifluoromethylbenzimidazolidine
2-amino-5-bromo-6-sulfamylbenzimidazolidine
5-chloro-2-guanidino-6-sulfamylbenzimidazolidine
2-guanidino-6-sulfamyl-5-trifluoromethylbenzimidazolidine
5-bromo-2-guanidino-6-sulfamylbenzimidazolidine
2-amino-5-chloro-6-sulfamyl-1-(3-tolyl)-1H-benzimidazole
2-amino-6-sulfamyl-1-(3-tolyl)-5-trifluoromethyl-1H-benzimidazole
2-amino-5-bromo-6-sulfamyl-1-(3-tolyl)-1H-benzimidazole
2-amino-5-chloro-6-sulfamyl-1-(4-tolyl)-1H-benzimidazole
2-amino-6-sulfamyl-1-(4-tolyl)-5-trifluoromethyl-1H-benzimidazole
2-amino-5-bromo-6-sulfamyl-1-(4-tolyl)-1H-benzimidazole
2-amino-5-chloro-1-(2,6-dimethylphenyl)-6-sulfamyl-1H-benzimidazole
2-amino-1-(2,6-dimethylphenyl)-6-sulfamyl-5-trifluoromethyl-1H-benzimidazole
2-amino-5-bromo-1-(2,6-dimethylphenyl)-6-sulfamyl-1H-benzimidazole
2-amino-5-chloro-6-sulfamyl-1-(2-tolyl) benzimidazolidine
2-amino-6-sulfamyl-1-(2-tolyl)-5-trifluoromethylbenzimidazolidine
2-amino-5-bromo-6-sulfamyl-1-(2-tolyl) benzimidazolidine
5-chloro-2-guanidino-6-sulfamyl-1-(2-tolyl) benzimidazoldine
2-guanidino-6-sulfamyl-1-(2-tolyl)-5-trifluoromethylbenzimidazolidine
5-bromo-2-guanidino-6-sulfamyl-1-(2-tolyl) benzimidazolidine
2-amino-5-chloro-1-(2-methoxyphenyl)-6-sulfamyl-1H-benzimidazole
2-amino-1-(2-methoxyphenyl)-6-sulfamyl-5-trifluoromethyl-1H-benzimidazole
2-amino-5-bromo-1-(2-methoxyphenyl)-6-sulfamyl-1H-benzimidazole
2-amino-5 chloro-1-(2-methoxyphenyl)-6-sulfamyl-1H-benzimidazole
2-amino-1-(2-chlorophenyl)-6-sulfamyl-5-trifluoromethyl-1H-benzimidazole
2-amino-5-bromo-1-(2-chlorophenyl)-6-sulfamyl-1H-benzimidazole
5-chloro-1-(2-chlorophenyl)-2-guanidino-6-sulfamyl-1H-benzimidazole
1-(2-chlorophenyl)-2-guanidino-6-sulfamyl-5-trifluoromethyl-1H-benzimidazole
5-bromo-1-(2-chlorophenyl)-2-guanidino-6-sulfamyl-1H-benzimidazole
2-amino-5-chloro-1-(2-chlorophenyl)-6 sulfamylbenzimidazolidine
2-amino-1-(2-chlorophenyl)-6-sulfamyl-5-trifluoromethylbenzimidazolidine
2-amino-5-bromo-1-(2-chlorophenyl)-6-sulfamylbenzimidazolidine
5-chloro-1-(2-chlorophenyl)-2-guanidino-6 sulfamylbenzimidazolidine.
1-(2-chlorophenyl)-2-guanidino-6-sulfamyl-5-trifluoromethylbenzimidazolidine
5-bromo-1-(2-chlorophenyl)-2-guanidino-6-sulfamylbenzimidazolidine
5-chloro-2-(furfurylamino)-6-sulfamyl-1H-benzimidazole
2-(furfurylamino)-6-sulfamyl-5-trifluoromethyl-1H-benzimidazole
5-chloro-2-(furfurylamino)-6-sulfamylbenzimidazolidine
2-(furfurylamino)-6-sulfamyl-5-triflouromethylbenzimidazolidine
5-chloro-6-sulfamyl-2-(2-tolyl)-1H-benzimidazole
2-(2-tolyl)-6-sulfamyl-5-trifluoromethyl-1H-benzimidazole
5-chloro-6-sulfamyl-2-(2-tolyl) benzimidazolidine
6-sulfamyl-2-(2-tolyl)-5-trifluoromethylbenzimidazolidine
5-chloro-6-sulfamyl-2-(3-tolyl)-1H-benzimidazole
6-sulfamyl-2-(3-tolyl)-5-trifluoromethyl-1H-benzimidazole
5-chloro-2-phenyl-6-sulfamyl-1H-benzimidazole
2-phenyl-6-sulfamyl-5-trifluoromethyl-1H-benzimidazole
5-chloro-6-sulfamyl-2-(3-tolyl) benzimidazolidine
6-sulfamyl-2-(3-tolyl)-5-trifluoromethylbenzimidazolidine
5-chloro-2-phenyl-6-sulfamylbenzimidazolidine
2-phenyl-6-sulfamyl-5-trifluoromethylbenzimidazolidine
2-(3-carboxy-4-hydroxy) anilino-6-sulfamyl-5-trifluoromethyl-1H-benzimidazole
2-(3-carboxy-4-hydroxy) anilino-5-chloro-6-sulfamyl-1H-benzimidazole
5-bromo-2-(3-carboxy-4-hydroxy) anilino-6-sulfamyl-1H-benzimidazole
2-(4-carboxy-3-hydroxy) anilino-5-chloro-6-sulfamyl-1H-benzimidazole
2-(4-carboxy-3-hydroxy) anilino-6-sulfamyl-5-trifluoromethyl-1H-benzimidazole
5-bromo-2-(4-carboxy-3-hydroxy) anilino-6-sulfamyl-1H-benzimidazole 5-chloro-2-(N$^3$-methylguanidino)-6-sulfamyl-1H-benzimidazole 5-bromo-2-(N$^3$-methylguanidino)-6-sulfamyl-1H-benzimidazole 2-(N$^3$-methylguanidino)-6-sulfamyl-5-trifluoromethyl-1H-benzimidazole 5-chloro-2-(N$^3$-methylguanidino)-6-sulfamyl-1-(2-tolyl)-1H-benzimidazole 5-bromo-2-(N$^3$-methylguanidino)-6-sulfamyl-1-(2-tolyl)-1H-benzimidazole 2-(N$^3$-methylguanidino)-6-sulfamyl-1-(2-tolyl)-5-trifluoromethyl-1H-benzimidazole 5-bromo-2-(N$^3$-methylguanidino)-6-sulfamylbenzimidazolidine 5-chloro-2-(N$^3$-methylguanidino)-6-sulfamyl-1-(2-tolyl)-benzimidazolidine 2-benzyl-5-chloro-6-sulfamyl-1H-benzimidazole hydrochlorid monohydrate 5-chloro-2-methyl-6-sulfamyl-1H-benzimidazole hydrochloride 5-chloro-6-sulfamyl-2-trifluoromethyl-1H-benzimidazole 5-chloro-6-sulfamyl-2-thiomethoxymethyl-1H-benzimidazole 5-chloro-2-propyl-6-sulfamyl-1H-benzimidazole 5-chloro-2-isopropyl-6-sulfamyl-1H-benzimidazole 5-chloro-2-ethyl-6-sulfamyl-1H-benzimidazole 2-butyl-5-chloro-6-sulfamyl-1H-benzimidazole

DESCRIPTION OF THE PREFERRED EMBODIMENTS

The following examples are given to illustrate the production of compounds according to the invention. The scope of the invention is not, however, meant to be limited to the specific details of the examples.

EXAMPLE 1

Preparation of 3-Chloroacetanilide (II)

To 500 g. of 3-chloroaniline (I) suspended in 4.5 l. of water heated at 35° was added stream wise 690 g. of acetic anhydride over a 40 minute period. After the addition, the reaction was stirred for 4 hours, filtered, and the product washed with 12 l. of water and dried to provide 620.2 g. of 3-chloroacetanilide (II) as white crystals, m.p. 72.5°–73° C.

Preparation of 5-Chloro-2-Nitroacetanilide (III)

To 100 g. of 3-chloroacetanilide (II) in 110 ml. of acetic acid and 120 ml. of acetic anhydride was added dropwise at −10° C. to −5° C. 44 ml. of 90% fuming nitric acid in 50 ml. of glacial acetic acid. After completion of the addition, the yellow solution was stirred for one hour at 0° to ±5° C. and then decanted into ice water. The yellow solid was collected by filtration, stirred 30 minutes with water, filtered, and then stirred 20 minutes with 1 l. of ether and filtered. Drying of the solid provided 110 g. of 5-chloro-2-nitroacetanilide (III) as a light tan solid, m.p. 114°–116° C.

Preparation of 5-Chloro-2-Nitroaniline (IV)

To 3 l. of absolute methanol was slowly added 2.4 g. of sodium. When all the sodium had dissolved, 68 g. of 5-chloro-2-nitroacetanilide was added with stirring and the solution refluxed for 7 hours. The solution was allowed to sit overnight and then concentrated in vacuo until crystals formed. Filtration of the precipitate provided 51 g. of 5-chloro-2-nitroaniline (IV) as yellow needles, m.p. 124°–126° C.

Preparation of 5-Chloro-2-Nitro-4-Sulfamylaniline (V)

To 235 ml of chlorosulfonic acid at 2° to 10° was added portion wise 83.0 g. of 5-chloro-2-nitroaniline (IV). After the addition, the dark brown solution was stirred at 96° to 98° C. for one hour, cooled, and carefully decanted into 2 l. of ice. The precipitate was collected by filtration, washed with 1 l. of water, and air dried. To 365 ml. of 30% ammonium hydroxide was added in 4 portions the crude sulfamyl chloride. The suspension was stirred for two hours at ambient temperature, cooled and set overnight. Filtration of the precipitate followed by recrystallization from ethanol provided 30 g. of 5-chloro-2-nitro-4-sulfamylaniline (V) as light yellow crystals, m.p. 249°–251° C.

Preparation of 2-Amino-5-Chloro-4-Sulfamylaniline (VI)

To 300 ml. of absolute methanol was added 19.25 g. of 5-chloro-2-nitro-4-sulfamylaniline (V). After flushing with nitrogen, 5.5 g. of 5% palladium on carbon was added and the mixture hydrogenated for two hours after which time no more hydrogen was taken up. The reaction was filtered, the charcoal washed with 100 ml. of absolute methanol, the filtrate concentrated to yield 10.4 g. of crude product. Recrystallization from ethanol treated with activated carbon provided 10.4 g. of 2-amino-5-chloro-4-sulfamylaniline (VI) as brown needles, m.p. 216° C.

Preparation of 2-Amino-5-Chloro-6-Sulfamyl-1H-Benzimidazole Hydrobromide (VII)

To 19.38 g. of cyanogen bromide in 408 ml. of water at 5° to 10° C. was added portion wise 15 g. of 2-amino-4-chloro-5-sulfamylaniline (VI). The suspension was stirred at ambient temperature for two hours and then set overnight. After concentrating the reaction mixture in vacuo, the residue was dissolved in boiling ethanol and filtered to remove some insoluble material. The ethanol solution was treated with charcoal, boiled, filtered, concentrated to 200 ml. and cooled. Dilution with ether followed by ice cooling precipitated the product as off-white crystals which upon drying provided 7.30 g. of 2-amino-5-chloro-6-sulfamyl-1H-benzimidazole hydrobromide (VII), m.p. 317° C.

Analysis: Calculated for C$_7$H$_8$Br Cl N$_4$O$_2$S: 25.66% C; 2,46%H; 17.10%N; 9.79%S; Found: 25.78%C; 2.52%H; 17.25%N; 9.60%S.

mmr: (DMSO-d$_6$-CDCl$_3$): 7.55 (bd, 4H), 7.78 (S, 1H), 8.18 (S, 1H), and 8.958 (bd, 2H)

ir (K Br) 1680 cm$^{-1}$ (NH$_2$)

Tlc (Silica gel): R$_f$=0.60, methanol as eluant.

EXAMPLE 2

Preparation of 5-Chloro-2 Guanidino-6-Sulfamyl-1H-Benzimidazole Hydrochloride (VIIII)

The procedure for making compound (VI) is the same as given in Example 1. A mixture of 2.22 g. of 2-amino-4-chloro-5-sulfamylaniline (VI) 0.84 g. of cyanoguanidine, 2 ml. of concentrated hydrochloric acid, and 8 ml. of water was refluxed for four hours. The reaction was concentrated in vacuo to a dark blue solid which was dissolved in methanol, treated with charcoal, boiled 5 minutes, filtered, cooled, and then filtered through Celite. Dilution with ether followed by ice cooling provided 0.2 g. of 5-chloro-2 guanidino-6-sulfamyl-1H-benzimidazole hydrochloride (VIII) as off-white crystals, m.p. 291°–292° C.

Analysis: Calculated for $C_8H_{10}Cl_2N_6O_2S$: 29.55%C; 3.10%H; 21.81%Cl; 25.85%N; 9.86%S; Found: 29.42%C; 3.17%H; 21.97%Cl; 25.67%N; 9.70%S ir (K Br) 1630, 1685 cm$^{-1}$ (NCNH$_2$)

Tlc (Silica gel): $R_5$=0.55, methanol as eluant.

Thearpeutically effective salts of the compounds of the invention may be made by methods which are per se known in the art and the resulting salts are also useful as diuretics and antihypertensive agents. The most suitable salts are the acid addition salts of the compounds with physiologically compatible acids to product, for example, the sulfates, hydrochlorides, hydrobromides, phosphates, cyclohexyl sulfamates, meleates, citrates, tartrates, succinates, ethane disulfonates, etc. The diuretic effectiveness of the compounds of the invention was confirmed by pharmacological tests run on selected compounds. For example, intravenous administration of compound (VIII) to male Sprague Dawley rats, compared to rats receiving equal volumes of saline indicated greater urine volume, greater sodium excretion and greater chloride excretion in the case of the animals to which the compound of the invention was administered.

EXAMPLE 3

Preparation of
5-Chloro-2-Phenyl-6-Sulfamyl-1H-Benzimidazole

A mixture of 2.21 g. of 2-amino-4-chloro-5-sulfamylaniline (VI), 50 ml. of glacial acetic acid, and 1.05 g. of benzaldehyde was refluxed for 16 hours and then decanted into water. The precipitate was collected by filtration, dissolved in ethanol, treated with Darco, filtered through filter paper and then through Celite. Concentration in vacuo provided a solid which was dissolved in ethanol, filtered, and forced out with water. Treatment of this beige solid with boiling acetonitrile provided an off-white solid mp 314°–316°.

Analysis: Calculated for $C_{13}H_{10}ClN_3O_2S$: 50.73%C; 3.28%H; 13.65%N; Found: 50.61%C; 3.54%H; 13.40%N

EXAMPLE 4

Preparation of
5-chloro-2-N$^3$-methylguanidino-6-sulfamyl-1H-benzimidazole hydrochloride To 2.22 g. of 2-amino-4-chloro-5-sulfamylaniline (VI) in 12 ml. of water was added 2 ml. of concentrated hydrochloric acid and 2 ml. of methanol. After adding 1.23 g. of N-methyl-cyanoguanidine, the dark solution was refluxed for 45 minutes, cooled, and the resultant solid collected by filtration. The solid was dissolved in methanol and filtered. Darco was added to the filtrate and the suspension boiled 10 minutes, filtered through filter paper, cooled and filtered through Celite. Dilution with ether provided a pink solid which, upon drying, yielded 0.5 g. of light pink solid, mp 284°–286°.

Analysis: Calculated for $C_9H_{12}Cl_2N_6O_2S$: 31.86%C; 3.57%H; 24.78%N; 9.45%S; Found: 31.44%C; 3.58%H; 24.58%N; 9.62%S in (KBr) 1680 cm$^{-1}$ (NH$_2$)

Tlc (Silica gel): R=0.10 ethyl acetate as eluant.

EXAMPLE 5

Preparation of
5-Chloro-2-Methyl-6-Sulfamyl-1H-Benzimidazole Hydrochloride

To 10 ml of 4 N hydrochloric acid containing 0.86 ml of acetic acid was added 2.22 g. of 2-amino-4-chloro-5-sulfamylaniline (VI) and the mixture refluxed for four hours. Concentration in vacuo gave a blue solid which was collected by filtration, dissolved in methanol, treated with charcoal and filtered. The blue solution was concentrated in vacuo and triturated with ether to yield a blue solid. Washing with methanol provided the product as light blue crystals which upon drying gave 1.0 g. of 5(6)-chloro-2-methyl-6(5)-sulfamyl-1(3)H-benzimidazole hydrochloride, m.p. 313°–316° C.

Analysis: Calculated for $C_8H_9Cl_2N_3O_2S$: 34.05%C; 3.21%H; 14.89%N; Found: 34.13%C; 3.47%H; 14.55%n

EXAMPLE 6

Preparation of 5-Chloro-Benzimidazole-6-Sulfonamide

In a round bottomed flask equipped with a condenser 24.0 g of 2-amino-4-chloro-5-sulfamyl-aniline and 7.0 g of formic acid is refluxed at 100° C. for two hours. Concentrate under vacuum. Dissolve in hot methanol, stir, cool and filter off the solid wt.=11.0 gm. m.p. 243.8° C.

| Anal. Calc. % | Found % |
|---|---|
| C = 36.29 | C = 36.32 |
| H — 2.61 | H = 2.60 |
| N — 18.14 | N = 17.91 |

EXAMPLE 7

Preparation of
5-Chloro-2-(2-Furyl)-6-Sulfamyl-1H-Benzimidazole

To 11.1 g of 2-amino-4-chloro-5-sulfamylaniline (VI) in 500 ml of isopropanol was added 2-furancarboxaldehyde followed by the addition of 6.00 g of p-benzoquinone. The dark mixture was covered with aluminum foil and refluxed for six hours. Concentration in vacuo provided a solid which upon recrystallization from one to one methanol-water gave 5.20 g of 5(6)-chloro-2-(2-furyl-6(5)-sulfamyl-1(3)H-benzimidazole as brown crystals, m.p. 308°–310°.

Analysis: Calculated for $C_{11}H_8CLN_3O_3S$: 44.38%C; 2.71%H; 14.11%N; 10.77%S; Found: 44.57%C; 2.91%H; 14.09%N; 10.92%S

EXAMPLE 8

Preparation of
2-Acetylamino-5-Chloro-Benzimidazole-6-Sulfonamide

In a round bottomed flask equipped with a stirrer place 21.2 gm of cynobromide. While stirring, add slowly 2.35 gm of Compound I. Continue stirring for 3 hours. It forms a brown suspension. Filter and concentrate the filtrate to about 200 cc. Add 43 cc of 2 N Sodium hydroxide to bring the pH to 75.8. To the resulting residue, add 50 cc of methanol. Combine all the solid and the solution and extract it with ethylacetate. Concentrate the extract to give 13.2 gm of solid. Dissolve it in ethylene glycol monomethyl ether. Add about 150 cc of acetic acid and reflux for 28 hours and concentrate it to a small volume. Reflux again for 28 hours, cool, filter off the solid, wash with hot acetic acid and dry to give 11.4 gm of Compound II. M.P. 341°–342° C.

| Anal. Calc. % | Found % |
|---|---|
| C = 33.68 | C = 34.09 |
| H = 2.81 | H = 2.87 |
| N = 17.46 | N = 17.60 |
| S = 9.98 | S = 9.85 |
| Cl = 11.07 | Cl = 11.27 |

EXAMPLE 9

Preparation of
2,5-Dichloro-6-sulfamyl-1H-Benzimidazole Hydrochloride Monohydrate A mixture of 1.50 g. 2-amino-4-chloro-5-sulfamylaniline and 0.50 g of urea was ground in a mortar and then heated in an oil bath at 170° under nitrogen for six hours. The resultant solid was dissolved in 50% ethanol-methanol and brought to a boil; charcoal was carefully added, the solution boiled ten minutes and filtered. Concentration in vacuo provided a solid which upon trituration with acetonitrile gave 0.8 g. of 5(6)-chloro-2-hydroxy-6(5)-sulfamyl-1(3H)-benzimidazole as light pink crystals, mp. 320°–322°.

ir: (K Br) Strong absorption at 1700 cm$^{-1}$

To 5 ml of phosphorus oxychloride was added 0.80 g of 5(6)-chloro-2-hydroxy-6(5)-sulfamyl-1(3)H-benzimidazole and the solution refluxed for six hours. Upon cooling, the reaction was diluted with benzene and filtered to yield a green solid. The solid was washed twice with 30 ml of anhydrous ether to provide 2,5(6)-dichloro-6(5)-sulfamyl-1(3)H-benzimidazole hydrochloride monohydrate as greenish colored crystals, mp. 275°–277°.

Analysis: Calculated for $C_7H_8Cl_3N_3O_3S$: 26.22%C; 2.52%H; 13.11%N; Found: 26.57%C; 2.66%H; 13.28%N

EXAMPLE 10

Preparation of
5-Chloro-2-propyl-6-sulfamyl-1H-Benzimidazole

A mixture of 9.0 g of 2-amino-4-chloro-5-sulfamyl aniline, 14.1 g of butyric acid, and 40.3 ml of a 15% hydrochloric acid solution was refluxed for 6 hours and then concentrated in vacuo to a solid. The solid was dissolved in hot methanol, treated with charcoal, boiled ten minutes, and filtered. Concentration in vacuo provided a solid which was then added portionwise to 200 ml of concentrated ammonium hydroxide. The free base was then recrystallized from acetonitrile to yield 4.5 g of pink crystals, m.p. 230°–234°.

EXAMPLE 11

Preparation of
2-Benzyl-5-Chloro-6-Sulfamyl-1H-Benzimidazole Hydrochloride Monohydrate A mixture of 12.0 g of 2-amino-4-chloro-5-sulfamylaniline, 29.5 g of phenylacetic acid, and 54.5 ml of a 15% hydrochloric acid solution was refluxed for 6 hours and the blue precipitate collected by filtration. The crude product was dissolved in hot methanol and the organic solvent then treated with charcoal. Filtration followed by conc. in vacuo gave crystals which upon trituration with methanol and drying provided 8.2 g of pink crystals, m.p. 176°–180° C.

Analysis calculated for $C_{14}H_{15}Cl_2N_3O_3S$: C 44.68%; H 4.02%; Cl 18.85%; N 11.17%; Found C 44.65%; H 4.18%; Cl 18.47%; N 11.10%;

EXAMPLE 12

Preparation of
5-Chloro-6-Sulfamyl-2-Thiomethoxymethyl-1H-Benzimidazole

To 50 ml of 4 N hydrochloric acid was added 11.8 g of 2-amino-4-chloro-5-sulfamyl aniline and 6.9 g of (methylthio)acetonitrile. After refluxing for 6 hours, the resulting precipitate was collected by filtration and then added with stirring to 150 ml of 38% ammonium hydroxide. The pink solid was collected by filtration and then suspended in water at 65°; the suspension was stirred for thirty minutes. The solid was dissolved in methanol, the solution brought to a boil, charcoal added, and the suspension then filtered, cooled and filtered through Celite. Recrystallization from acetronitrile provided 2.5 g of crystals, mp 234°–237°.

Analysis calculated for $C_9H_{10}ClN_3O_2S_2$: C 37.04%; H 3.45%; Cl 12.15%; N 14.40%; S 21.98%; Found C 36.92%; H 3.38%; Cl 11.98%; N 14.33%; S 21.62%

EXAMPLE 13

Preparation of
2-n-Butyl-5(6)-Chloro-6(5)-Sulfamyl-1(3)H-Benzimidazole

A suspension of 11.80 g of 2-amino-4-chloro-5-sulfamylaniline, 8.10 g of valeric acid, and 50 ml of 4 N hydrochloric acid was refluxed for 6 hours. The precipitate was collected by filtration and then added with stirring to 200 ml of 38% ammonium hydroxide; the resulting solid was then collected and suspended in 60° water with stirring for twenty minutes. Recrystallization from acetonitrile provided upon drying 8.6 g of colorless crystals, mp 208°–210°.

Analysis calculated for $C_{11}H_{14}ClN_3O_2S$: C 45.90%; H 4.90%; Cl 12.32%; N 14.60%; Found: C 46.12%; H 5.01%; Cl 12.30%; N 14.51%

EXAMPLE 14

Preparation of
5(6)-Chloro-2-Trifluoromethyl-6(5)-Sulfamyl-1(3)H-Benzimidazole

To 10 ml of 4 N hydrochloric acid was added 2.22 g of 2-amino-4-chloro-5-sulfamyl aniline followed by 1.70 g of trifluoroacetic acid and the suspension refluxed for 6 hours. The solid was collected by filtration and then dissolved in 80 ml of methanol. After adding charcoal, the suspension was boiled for five minutes, filtered, cooled, and then filtered through Celite. Concentration in vacuo provided a pink solid which upon recrystallization from acetonitrile gave 0.5 g of off-white crystals, m.p. 282°–285°.

Analysis calculated for $C_8H_5ClF_3N_3O_2S$: C 32.06%; H 1.68%; N 14.02%; Found: C 32.11%; H 1.82%; N 13.84%

EXAMPLE 15

Preparation of
5-Chloro-2-Ethyl-6-Sulfamyl-1H-Benzimidazole

A mixture of 12.0 g of 2-amino-4-chloro-5-sulfamylaniline, 16.1 g of propionic acid, and 54.4 ml of 4

N hydrochloric acid was refluxed for 6 hours. The solid was collected by filtration, dissolved in boiling methanol, charcoal added, and the solution filtered through Celite. Upon adding to 38% ammonium hydroxide with stirring, a pink solid formed. This was collected by filtration, washed with hot water, air dried, and then recrystallized from acetonitrile to provide 2.0 g of crystals, m.p. 240°–242°.

Analysis calculated for $C_9H_{10}ClN_3O_2S$: C 41.62%; H 3.88%; Cl 13.65%; N 16.18%; Found: C 41.32%; H 3.88%; Cl 13.30%; N 16.14%

EXAMPLE 16

Preparation of 5-Chloro-2-Hydroxymethyl-6-Sulfamyl-1H-Benzimidazole

To 11.0 g of 2-amino-4-chloro-5-sulfamylaniline in 50 ml of 4 N hydrochloric acid was added 5.6 g of glycolic acid. After refluxing for 6 hours, the resulting solid was collected by filtration and then added with stirring to 200 ml of 38% ammonium hydroxide; the pink precipitate was then collected and suspended in water with stirring at 60° for 20 minutes. Recrystallization of the solid from methanol provided 3.0 g of colorless crystals, m.p. 247°–250°.

Analysis calculated for $C_8H_8ClN_3O_2S$: C 36.71%; H 3.08%; Cl 13.55%; N 16.06%; Found: C 36.53%; H 3.04%; Cl 13.49%; N 16.17%

EXAMPLE 17

Preparation of 5-Chloro-2-Pentyl-6-Sulfamyl-1H-Benzimidazole

To 50 ml of 4 N hydrochloric acid containing 11.8 g of 2-amino-4-chloro-5-sulfamylaniline was added 9.2 g of hexanoic acid and the suspension refluxed for 6 hours. Concentration in vacuo provided a solid which was then slowly added with stirring to 100 ml of 38% ammonium hydroxide. After collecting the solid by filtration, the precipitate was added to 400 ml of methanol and the suspension brought to a boil. Charcoal was then added and the mixture filtered through filter paper, cooled, and filtered through Celite. Concentration in vacuo gave brown crystals which upon recrystallization from acetonitrile provided 2.6 g of product, mp 183°–185°.

Analysis calculated for $C_{12}H_{16}ClN_3O_2S$: C 47.75; H 5.34; N 13.92; Cl 11.75; Found: C 47.46; H 5.28; N 13.66; Cl 11.55

EXAMPLE 18

Preparation of 5-Chloro-2-Dichloromethyl-6-Sulfamyl-1H-Benzimidazole

To 11.8 g of 2-amino-4-chloro-5-sulfamyl aniline in 50 ml of 4 N hydrochloric acid was added 20.5 g of dichloroacetic acid and the suspension refluxed for 6 hours. Concentration in vacuo provided a dark viscous oil which was suspended in 150 ml of water and crystallized through vigorous scratching. The dark brown solid was then dissolved in methanol, the solution brought to a boil, and charcoal added. After boiling for five minutes, the suspension was filtered through filter paper, cooled and then filtered through Celite. Concentration in vacuo gave a viscous oil which upon setting at ambient temperature for 48 hours crystallized. Tritration with acetonitrile provided 4.5 g of beige crystals, m.p. 225°–227°.

Analysis calculated for $C_8H_6Cl_3N_3O_2S$: C 30.54; H 1.92; N 13.36; Cl 33.81; Found: C 30.84; H 2.13; N 13.62; Cl 33.74

EXAMPLE 19

Preparation of 5-Chloro-2-Chloromethyl-6-Sulfamyl-1H-Benzimidazole

To 50 ml of 4 N hydrochloric acid containing 11.8 g 2-amino-4-chloro-5-sulfamylaniline was added 7.5 g of chloroacetic acid and the suspension was refluxed for 6 hours. The precipitate was collected by filtration, dissolved in hot methanol, and the solution boiled with charcoal for ten minutes. Cooling and filtration through Celite followed by concentration of the filtrate provided 8.0 g of off-white crystals, m.p. 296°–301°.

Analysis calculated for $C_8H_8Cl_3N_3O_2S$: C 30.35; H 2.55; N 13.27; Cl 33.60; S 10.13; Found: C 30.60; H 2.63; N 13.12; Cl 32.78; S 10.33

EXAMPLE 20

Preparation of 5-Chloro-2-Isopropyl-6-Sulfamyl-1H-Benzimidazole

To 50 ml of 4 N hydrochloric acid containing 11.8 g of 2-amino-4-chloro-5-sulfamylaniline was added 7.0 g of isobutyric acid and the suspension refluxed for 6 hours. The mixture was concentraded in vacuo to a solid and the solid then added with stirring to 38% ammonium hydroxide and stirred for thirty minutes at 50° C. The solid was collected by filtration, air dried, dissolved in isopropanol, and charcoal added. After boiling for five minutes, the suspension was filtered, cooled, and then filtered through Celite. Recrystallization from isopropanol provided 2.0 g of off-white crystals, mg 256°–259°.

Analysis calculated for $C_{10}H_{13}ClN_3O_2S$: C 43.71%; H 4.77; N 15.29; Cl 12.91; Found: C 43.91%; H 4.41; N 15.49; Cl 12.75

EXAMPLE 21

Preparation of 5-Chloro-2-Phenethyl-6-Sulfamyl-1H-Benzimidazole

To 40 ml of 4 N hydrochloric acid containing 9.4 g of 2-amino-4-chloro-5-sulfamylaniline was added 9.5 g of hydrocinnamic acid and the mixture refluxed for 6 hours. The dark reaction mixture was concentrated in vacuo to a semi-solid which was then added with stirring to 200 ml of 38% ammonium hydroxide. After stirring for thirty minutes, the solid was collected by filtration and then suspended in 200 ml of water at 50° C. Upon stirring for thirty minutes, the product was collected by filtration, dissolved in methanol, and the solution treated with charcoal and boiled for five minutes. The suspension was cooled, filtered through Celite, and concentrated in vacuo to yield pink crystals. Recrystallization from acetonitrile provided 2.6 g of off-white crystals, mp 226°–228°.

Analysis calculated for $C_{15}H_{14}ClN_3O_2S$: C 53.65; H 4.20; N 12.51; Cl 10.56; Found: C 53.65; H 4.40; N 12.64; Cl 10.99

EXAMPLE 22

Preparation of 5-Chloro-2-Mercapto-6-Sulfamyl-1H-Benzimidazole

To 2.9 g of potassium hydroxide dissolved in 45 ml of ethanol and 9 ml of water was added with stirring 4.0 g of carbon disulfide. This solution was then added dropwise to 300 ml of ethanol containing 11.8 g of 2-amino-4-chloro-5-sulfamylaniline. The reaction was refluxed for 5 hours and then concentrated in vacuo to a dark oil. Treatment with 50° C. water provided a solid which was removed by filtration. The filtrate was cooled with ice and acidified to pH 5.0 with acetic acid to yield a gray solid. Trituration of the solid with boiling methanol provided a solid which upon drying gave 5.6 g of pink crystals, m.p. 341°–343°.

Analysis calculated for $C_7H_6ClN_3O_2S_2$: C 31.88; H 2.29; N 15.93; S 24.32; Cl 13.45; Found: C 31.22; H 2.58; N 15.80; S 24.06; CL 13.82

EXAMPLE 23

Preparation of 5-Chloro-2-(2-Methylbenzyl)-6-Sulfamyl-1H-Benzimidazole

To 50 ml of 6 N hydrochloric acid was added 11.8 g of 2-amino-4-chloro-5-sulfamylaniline and 10.4 g of 2-methylbenzyl cyanide. The reaction was refluxed for 22 hours and then concentrated in vacuo to a solid which was then added with stirring to 200 ml of 38% ammonium hydroxide. Filtration provided the free base as a semi-gum which was dissolved in 500 ml of methanol. The methanol solution was brought to a boil, charcoal added, and boiling continued for five minutes. Upon cooling, the suspension was filtered through Celite and the filtrate concentrated in vacuo to yield a solid, m.p. 226°–230°.

Analysis calculated for $C_{15}H_{14}ClN_3O_2S$: C 53.65; H 4.20; N 12.51; Cl 10.56; S 9.55; Found: C 53.22; H 4.32; N 12.39; Cl 10.51; S 9.30

EXAMPLE 24

Preparation of 5-Chloro-2-Methylthio-6-Sulfamyl-1H-Benzimidazole

To 30 ml of ethanol containing 1.30 g of 5(6)-chloro-2-mercapto-6(5)-sulfamyl-1(3) H-benzimidazole was added 0.22 g of sodium hydroxide and the mixture brought to reflux. To this solution was added all at once 0.86 g of methyl iodide and the reaction then refluxed for one hour. The reaction was decanted into 60 ml of water prewarmed to 75° C.; crystals formed upon cooling. Drying provided 0.5 g of off-white crystals, mp 253°–254°. Analysis calculated for $C_8H_8ClN_3O_2S_2$: C 34.59; H 2.90; N 15.13; Cl 12.77; S 23.09; Found: C 34.41; H 2.79; N 15.08; Cl 12.96; S 23.22

EXAMPLE 25

Preparation of 5,5'-Dichloro-6,6'-Disulfamyl-2,2'-Bi-1H-Benzimidazole of the Formula

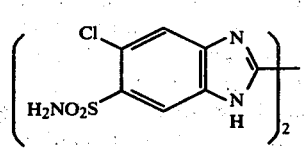

To 2.22 g of 2-amino-4-chloro-5-sulfamylaniline in 10 ml of 4 N hydrochloric acid was added 3.00 g trichloroacetic acid and the suspension refluxed for 6 hours. Filtration provided a green precipitate which was triturated with boiling methanol, filtered, and dried to yield 0.5 g of crystals, m.p. 360°.

Analysis calculated for $C_{14}H_{10}Cl_2N_6O_4S_2$: C 36.45; H 2.19; N 18.22; Cl 15.37; S 13.90; Found: C 36.14; H 2.34; N 18.11; Cl 15.77; S 13.77

EXAMPLE 26

Preparation of 5-Chloro-2-Phenoxymethyl-6-Sulfamyl-1H-Benzimidazole

2-Amino-4-chloro-5-sulfamyl aniline [22.15 gm 0.1 mole] and phenoxyacetic acid [15.2 gm, 0.1 mole] were ground to an intimate mix, then refluxed with 4 N hydrochloric acid [100 ml] for 4 hours. On cooling to room temperature the black solid was filtered, repeatedly triturated with water to remove color, then air dried.

The black solid was stirred at room temperature with ammonium hydroxide [40 ml] for 2 hours. The reprecipitated brown solid was filtered, air dried, triturated several times with ether to remove color and finally dried over boiling xylene and under vacuum for 4 hours. The brown solid [6.8 gm 20% yield] had mp 245°–248° C.

| Analysis Calculated for $C_{14}H_{12}ClN_3O_3S$: | | | | |
|---|---|---|---|---|
| C | H | Cl | N | S |
| 49.78 | 3.56 | 10.52 | 12.44 | 9.48 |
| Found 49.83 | 3.73 | 10.67 | 12.47 | 9.37 |

EXAMPLE 28

Preparation of 5-Chloro-2-(3-Phenylpropyl)-6-Sulfamyl-1H-Benzimidazole

To 16.5 g of 2-amino-4-chloro-5-sulfamylaniline in 75 ml of 6 N hydrochloric acid was added 18.2 g of 4-phenylbutyric acid and the mixture refluxed for 24 hours. The reaction was concentrated in vacuo to a semi-solid which was then added with stirring to 200 ml of concentrated ammonium hydroxide. The solid was collected by filtration and added to 200 ml of water at 50°. After collecting the product by filtration, the solid was dissolved in methanol, the methanol brought to a boil, charcoal added, and the suspension then filtered through two sheets of filter paper, and then through Celite. Concentration in vacuo provided a semi-solid which upon treatment with hot acetonitrile gave a solid (ammonium chloride) which was removed by filtration. The red filtrate was concentrated in vacuo to a viscous oil which upon treatment with acetonitrile gave 3.2 g of crystals, m.p. 105°–107°.

| Analysis calculated for $C_{16}H_{16}ClN_3O_2S$: | | | | |
|---|---|---|---|---|
| 54.93% | 4.61% | 12.02% | 9.16% | 10.13% |
| Found 54.57% | 4.57% | 11.79% | 9.44% | 10.31% |

EXAMPLE 29

Preparation of 5-Chloro-2-(2-Methylphenylethyl)-6-Sulfamyl-1H-Benzimidazole

To 11.5 g of 3-(2-methylphenyl)propionitrile in 50 ml of 6 N hydrochloric acid was added 11.8 g of 2-amino-4-chloro-5 sulfamylaniline and the suspension refluxed for 12 hours. The precipitate was collected by filtration and added with stirring to 200 ml of concentrated ammonium hydroxide. The free base was then collected and added to methanol; the methanol was brought to a boil, charcoal added, and the suspension filtered. Concentration in vacuo provided a semi-solid which upon treatment with acetonitrile gave a red solution and a precipitate (ammonium chloride). Concentration of the red solution in vacuo provided a solid which upon recrystallization from acetonitrile yielded off-white crystals, m.p. 205°–208°.

| Analysis Calculated for $C_{16}H_{16}ClN_3O_2S$ | | | |
|---|---|---|---|
| C | H | N | Cl |
| 54.92% | 4.61% | 12.01% | 10.14% |
| Found 54.92% | 4.82% | 11.84% | 10.16% |

EXAMPLE 30

Preparation of 5-Chloro-2-(4-Phenylbutyl)-6-Sulfamyl-1H-Benzimidazole

To 25 ml of 6 N hydrochloric acid was added 5.5 g of 2-amino-4-chloro-5-sulfamylaniline and 6.6 g of 5-phenylvaleric acid and the mixture refluxed for twenty-four hours. The gummy solid was collected by concentration in vacuo and then added to concentrated ammonium hydroxide. The suspension was stirred for twenty minutes, collected by filtration, and suspended in water at 50° C. The solid was collected by filtration, dissolved in methanol, brought to a boil, and charcoal added. The suspension was then filtered through two sheets of filter paper, cooled, and filtered through Celite. Recrystallization from acetonitrile provided 1.0 g of colorless crystals, m.p. 176°–180°.

| Analysis Calculated for $C_{17}H_{18}ClN_3O_2S$ | | |
|---|---|---|
| C | H | N |
| 56.11% | 4.99% | 11.55% |
| Found 55.98% | 4.75% | 11.67% |

EXAMPLE 31

Preparation of 5-Chloro-2-(2-Chlorobenzyl)-6-Sulfamyl-1H-Benzimidazole

To 150 ml of 8 N hydrochloric acid was added 13.3 g of 2-amino-4-chloro-5-sulfamylaniline and 8.6 g of o-chlorophenylacetic acid. The reaction was refluxed for 23 hours and the precipitate collected by filtration; the solid was added with vigorous stirring to 200 ml of concentrated ammonium hydroxide. The semi-solid was collected by filtration and then washed with 100 ml of water which was stirred at 50° C. for twenty minutes. After collecting the solid by filtration, the crystals were dissolved in methanol and the solution brought to a boil. Charcoal was added and the solution was boiled for five minutes, filtered through two sheets of filter paper, cooled, and then filtered through Celite. Concentration in vacuo gave a dark pink solid which upon recrystallization from acetonitrile provided 3.0 g of pink crystals, m.p. 223°–226°.

| Analysis Calculated for $C_{14}H_{11}Cl_2N_3O_2S$: | | | |
|---|---|---|---|
| C | H | N | Cl |
| 47.20% | 3.11% | 11.80% | 19.90% |
| Found 47.38% | 3.34% | 11.57% | 19.75% |

EXAMPLE 32

Preparation of 2-(4-Biphenylmethyl)-5-Chloro-6-Sulfamyl-1H-Benzimidazole

A mixture of 2.95 g of 2-amino-4-chloro-5-sulfamyaniline dihydrochloride and 6.0 g of 4-biphenylacetic acid was ground together and heated at 180°–200° C. for 5 hours, cooled, ground to a fine powder and added to 50 ml of concentrated ammonium hyroxide with stirring. After fifteen minutes, the resulting pink solid was collected by filtration. The solid was dissolved in 500 ml of methanol, brought to a boil, charcoal added, and the filtrate filtered through two sheets of filter paper and then through Celite. Concentration in vacuo provided a pink solid which upon recrystallization from acetonitrile provided 0.6 g of pink crystals, mp. 237°–240°.

| Analysis Calculated for $C_{20}H_{16}ClN_3O_2S$: | | | |
|---|---|---|---|
| C | H | N | Cl |
| 60.37% | 4.05% | 10.56% | 8.91% |
| Found 60.70% | 4.30% | 10.39% | 8.39% |

EXAMPLE 33

Preparation of 2-(1-Adamantanylmethyl)-5-Chloro-6-Sulfamyl-1H-Benzimidazole Hemihydrate A mixture of 1.6 g of 2-amino-4-chloro-5-sulfamylaniline dihydrochloride and 1.6 g of 1-adamantane acetic acid was heated at 180°–200° for 5 hours. The mixture was cooled and the solid collected and ground into a fine powder; this was then added slowly to 100 ml of concentrated ammonium hydroxide with stirring. After stirring for twenty minutes, the solid was collected by filtration and then added to 150 ml of methanol, brought to a boil, charcoal added, and boiling continued for five minutes. The mixture was filtered through two sheets of filter paper, cooled, filtered through Celite, and then concentrated in vacuo to a dark pink solid. Recrystallization from acetonitrile provided 0.5 g of product, m.p. 203°–205°.

| Analysis Calculated for $C_{18}H_{22}ClN_3O_2S \cdot \frac{1}{2}H_2O$: | | | |
|---|---|---|---|
| C | H | N | Cl |
| 55.58% | 5.96% | 10.80% | 9.12% |
| Found 55.11% | 6.07% | 10.96% | 8.69% |

EXAMPLE 34

Preparation of 5-Chloro-2-Difluoromethyl-6-Sulfamyl-1H-Benzimidazole

To 25 ml of 6 N hydrochloric acid containing 2.22 g of 2-amino-4-chloro-5-sulfamylaniline was added 1.50 g of difluoroacetic acid and the mixture refluxed for 12 hours. The resultant solid was collected by filtration and then added to concentrated ammonium hydroxide to yield the free base which was then suspended in water at 50° C. The solid was then collected by filtration, dissolved in methanol, the methanol brought to a boil, charcoal added, and the suspension filtered through two sheets of filter paper, and then through Celite. Concentration in vacuo provided a brown solid which upon recrystallization from acetonitrile yielded a pink solid, m.p. 233°–235°.

| Analysis Calculated for $C_8H_6ClF_2N_3O_2S$: | | | |
|---|---|---|---|
| C | H | F | N |
| 34.11% | 2.15% | 13.49% | 14.92% |
| Found 34.31% | 2.35% | 13.96% | 14.99% |

EXAMPLE 35

Preparation of 2-(2-Adamantanyl)-5-Chloro-6-Sulfamyl-1H-Benzimidazole Hemihydrate A mixture of 2.95 g of 2-amino-4-chloro-5-sulfamylaniline dihydrochloride and 2.70 g of 1-adamantanecarboxylic acid was ground together and heated at 190°–200° for 5 hours. The dark solid was dissolved in 500 ml of methanol, the methanol brought to a boil, charcoal added, boiling continued for five minutes, and the suspension then filtered through two sheets of filter paper, and then through Celite. Concentration in vacuo provided a solid which was then added to 100 ml of concentrated ammonium hydrozide and stirred for twenty minutes. The crude product was collected by filtration and recrystallized from acetonitrile to provide 0.5 g of colorless crystals, m.p. 207°–210°.

| Analysis Calculated for $C_{17}H_{20}ClN_3O_2S$: | | | |
|---|---|---|---|
| C | H | N | Cl |
| 54.45% | 5.65% | 11.21% | 9.46% |
| Found 54.22% | 5.69% | 11.10% | 8.69% |

EXAMPLE 36

Preparation of 5-Chloro-2-(4-Methylbenzyl)-6-Sulfamyl-1H-Benzimidazole

To 150 ml of 6 N hydrochloric acid was added 17.7 g of 2-amino-4-chloro-5-sulfamylaniline followed by the addition of 15.7 g of 4-methylbenzyl cyanide; the mixture was then refluxed for 9 hours. The precipitate was collected by filtration and added to 300 ml of concentration ammonium hydroxide. After stirring for ten minutes at ambient temperature, the solid was collected and then added to 300 ml of water and stirred at 40° C. for ten minutes. The crude product was collected and dissolved in 1 liter of methanol which was brought to a boil; after stirring for five minutes, charcoal was added, and stirring continued for ten more minutes. The mixture was then filtered through two sheets of filter paper and then through Celite. Concentration in vacuo provided a solid which upon recrystallization from acetonitrile provided 3.0 g of pink crystals, m.p. 214°–217°.

| Analysis Calculated for $C_{15}H_{14}N_3ClO_2S$: | | | |
|---|---|---|---|
| C | H | N | Cl |
| 53.64% | 4.20% | 12.51% | 10.56% |
| Found 53.62% | 4.22% | 12.65% | 10.75% |

The new compounds of the present invention can be mixed with any suitable pharmaceutical carrier, solid or liquid, to provide diuretic and antihypertensive compositions. These compositions can be made for oral administration or for administration by injection. The active ingredient can be in the form of the base compound or the pharmaceutically acceptable salt thereof.

What is claimed is:

1. A compound of the formula:

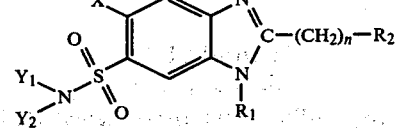

or

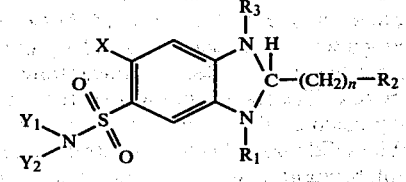

or a physiologically compatible salt thereof, wherein:

X=halogen or trifluormethyl, $Y_1$ and $Y_2$=independently hydrogen or lower alkyl, $R_1$=hydrogen, lower alkyl, furfuryl, phenyl substituted by lower alkyl, by lower alkoxy or by halogen, n=0 or an integer from 1–4, $R_2$=amino, hydrogen, hydroxyl, mercapto, lower alkyl mercapto, furyl, adamantanyl, halogen, lower alkyl, phenyl, phenyl substituted by lower alkyl, phenyl substituted by halogen, biphenyl, formamido, guanidino, guanidino substituted by lower alkyl and amino substituted by lower alkyl, by carboxy, by carboxy-lower alkyl, by lower alkylcarboxy, by phenyl, by phenyl substituted by carboxy, by phenyl substituted by hydroxy, by phenyl substituted by lower alkyl, by phenyl substituted by halogen, by furfuryl, and by carboxy substituted by phenoxy lower alkyl, and $R_3$=hydrogen, lower alkyl, phenyl or substituted phenyl substituted by lower alkyl, lower alkoxy or halogen.

2. The compound of the formula

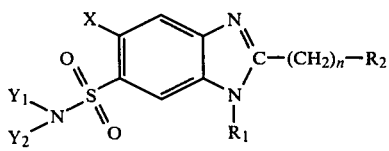

wherein X is halogen or trifluormethyl, wherein $Y_1$ and $Y_2$ are each hydrogen or lower alkyl, wherein $R_1$ is hydrogen, lower akyl, or substituted phenyl, substituted by lower alkyl, lower alkoxy or halogen, wherein n is 0 and wherein $R_2$ is amino, formamido or guanidino.

3. The compound of the formula

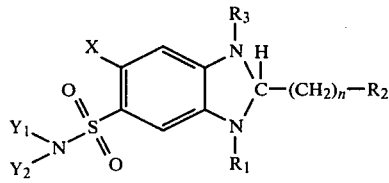

wherein X is halogen or trifluormethyl, wherein $Y_1$ and $Y_2$ are each hydrogen or lower alkyl, wherein $R_1$ is hydrogen, lower alkyl, or substituted phenyl substituted by lower alkyl, lower alkoxy or halogen, wherein n is 0 and wherein $R_2$ is amino, formamido or guanidino.

4. The compound of claim 2 wherein X is chlorine, $Y_1$ and $Y_2$ are each hydrogen, $R_1$ is hydrogen, n is 0 and $R_2$ is amino.

5. The compound of claim 2 wherein X is chlorine, $Y_1$ and $Y_2$ are each hydrogen, $R_1$ is hydrogen, n is 0 and $R_2$ is guanidino.

6. The compound 2-benzyl-5(6)-chloro-6(5)-sulfamyl-1(3)H-benzimidazole and salts thereof.

7. The compound of claim 1 wherein said compound is 5-chloro-2-methyl-6-sulfamyl-1H-benzimidazole and salts thereof.

8. The compound 5(6)-chloro-6(5)-sulfamyl-2-trifluoromethyl-1(3)H-benzimidazole.

9. The compound 5(6)-chloro-6(5)-sulfamyl-2-thiomethoxymethyl-1(3)H-benzimidazole.

10. The compound of claim 1 wherein said compound is 5(6)-chloro-2-propyl-6(5)-sulfamyl-1(3)H-benzimidazole.

11. The compound of claim 1 wherein said compound is 5(6)-chloro-2-isopropyl-6(5)-sulfamyl-1(3)H-benzimidazole.

12. The compound of claim 1 wherein said compound is 5(6)-chloro-2-ethyl-6(5)-sulfamyl-1(3)H-benzimidazole.

13. The compound of claim 1 wherein said compound is 2-butyl-5(6)-chloro-6(5)-sulfamyl-1(3)H-benzimidazole.

14. Diuretic composition, comprising a diuretic effective amount of the compound of claim 1 and a pharmaceutical carrier.

15. Antihypertensive composition, comprising an antihypertensive effective amount of the compound of claim 1 and a pharmaceutical carrier.

16. The method of achieving a diuretic effect, which comprises administering to a subject requiring the same a diuretic effective amount of a compound of the formula:

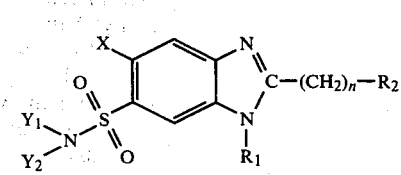

or

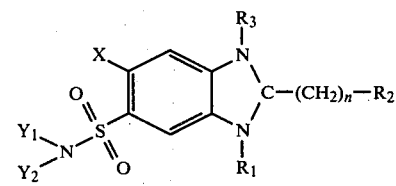

or a physiologically compatible salt thereof, wherein:
X = halogen or trifluormethyl,
$Y_1$ and $Y_2$ = independently hydrogen or lower alkyl,
$R_1$ = hydrogen, lower alkyl, furfuryl, phenyl substituted by lower alkyl, by lower alkoxy or by halogen,
n = 0 or an integer from 1–4,
$R_2$ = amino, hydrogen, hydroxyl, mercapto, lower alkyl mercapto, furyl, adamantanyl, halogen, lower alkyl, phenyl, phenyl substituted by lower alkyl, phenyl substituted by halogen, biphenyl, formamido, guanidino, guanidino substituted by lower alkyl and amino substituted by lower alkyl, by carboxy, by carboxy-lower alkyl, by lower alkylcarboxy, by phenyl, by phenyl substituted by carboxy, by phenyl substituted by hydroxy, by phenyl substituted by lower alkyl, by phenyl substituted by halogen, by furfuryl, and by carboxy substituted by phenoxy lower alkyl, and
$R_3$ = hydrogen, lower alkyl, phenyl or substituted phenyl, substituted by lower alkyl, lower alkoxy or halogen.

17. Method of achieving an antihypertensive effect, which comprises administering to a subject requiring the same an antihypertensive effective amount of a compound of the formula:

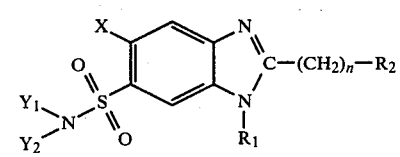

or

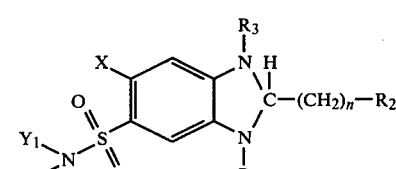

or a physiologically compatible salt thereof, wherein:
X = halogen or trifluormethyl,
$Y_1$ and $Y_2$ = independently hydrogen or lower alkyl,
$R_1$ = hydrogen, lower alkyl, furfuryl, phenyl substituted by lower alkyl, by lower alkoxy or by halogen,
n = 0 or an integer from 1–4, $R_2$ = amino, hydrogen, hydroxyl, mercapto, lower alkyl mercapto, furyl, adamantanyl, halogen, lower alkyl, phenyl, phenyl substituted by lower alkyl, phenyl substituted by halogen, biphenyl, formamido, guanidino, guanidino substituted by lower alkyl and amino substituted by lower alkyl, by carboxy, by carboxy-lower alkyl, by lower alkyl-carboxy, by phenyl, by phenyl substituted by carboxy, by phenyl substituted by hydroxy, by phenyl substituted by lower alkyl by phenyl substituted by halogen, by furfuryl, and by carboxy substituted by phenoxy lower alkyl, and $R_3$ = hydrogen, lower alkyl, phenyl or substituted phenyl, substituted by lower alkyl, lower alkoxy or halogen.

* * * * *